US008588936B2

(12) United States Patent
MacDonald et al.

(10) Patent No.: US 8,588,936 B2
(45) Date of Patent: Nov. 19, 2013

(54) SPINAL CORD STIMULATION SYSTEM AND METHODS OF USING SAME

(75) Inventors: Joel D. MacDonald, Salt Lake City, UT (US); Kirk Fisher, West Jordon, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 172 days.

(21) Appl. No.: 13/193,250

(22) Filed: Jul. 28, 2011

(65) Prior Publication Data

US 2012/0029528 A1 Feb. 2, 2012

Related U.S. Application Data

(60) Provisional application No. 61/368,501, filed on Jul. 28, 2010, provisional application No. 61/415,181, filed on Nov. 18, 2010.

(51) Int. Cl.
*A61N 1/00* (2006.01)
(52) U.S. Cl.
USPC .......................................... 607/116
(58) Field of Classification Search
USPC .............. 606/129, 130; 607/115, 116, 117; 600/373, 377
See application file for complete search history.

(56) References Cited

U.S. PATENT DOCUMENTS

| | | | |
|---|---|---|---|
| 4,779,616 A | 10/1988 | Johnson | |
| 5,501,692 A | 3/1996 | Riza | |
| 5,921,918 A | 7/1999 | Riza | |
| 6,221,070 B1 * | 4/2001 | Tu et al. | 606/41 |
| 6,249,707 B1 | 6/2001 | Kohnen | |
| 6,415,187 B1 | 7/2002 | Kuzma | |
| 6,522,932 B1 * | 2/2003 | Kuzma et al. | 607/116 |
| 7,801,615 B2 | 9/2010 | Meadows | |
| 7,949,412 B1 * | 5/2011 | Harrison et al. | 607/137 |
| 2005/0033315 A1 | 2/2005 | Hankins | |
| 2005/0203588 A1 | 9/2005 | King | |
| 2009/0062883 A1 * | 3/2009 | Meadows et al. | 607/46 |
| 2009/0204192 A1 * | 8/2009 | Carlton et al. | 607/116 |

FOREIGN PATENT DOCUMENTS

WO WO 2013/016615 1/2013

OTHER PUBLICATIONS

International Search Report mailed Oct. 16, 2012 for WO/2013/016615 (PCT/US2012/048490) filed Jul. 27, 2012 (Applicant: University Of Utah Research Foundation // Inventor: MacDonald) (2 pages).
U.S. Appl. No. 61/368,501, filed Jul. 28, 2010, MacDonald.
U.S. Appl. No. 61/415,181, filed Nov. 18, 2010, MacDonald.
Written Opinion mailed Oct. 16, 2012 for WO/2013/016615 (PCT/US2012/048490) filed Jul. 27, 2012 (Applicant: University Of Utah Research Foundation // Inventor: Macdonald) (6 pages).
Barolat G. 1993. Experience with 509 plate electrodes implanted epidurally from C1 to L1. Stereotact Funct Neurosurg. 61(2):60-79.

(Continued)

*Primary Examiner* — Tuan V Nguyen
(74) *Attorney, Agent, or Firm* — Ballard Spahr LLP

(57) ABSTRACT

A method for optimizing the stimulation of the dorsal column of the spinal cord is disclosed. The method includes providing a stimulating electrode array and a frame element. The frame element is configured to couple to the stimulating electrode array and guide the stimulating electrode array to a desired position proximate the dorsal column of the spinal cord of a subject.

18 Claims, 9 Drawing Sheets

(56) References Cited

OTHER PUBLICATIONS

Beems T, et al. 2007. Minimally invasive placement of epidural plate electrodes under local anaesthesia in spinal cord stimulation. Acta Neurochir Suppl. 97(Pt 1):105-109.

Beems T, et al. 2006. Use of a tubular retractor system as a minimally invasive technique for epidural plate electrode placement under local anesthesia for spinal cord stimulation: technical note. Neurosurgery. 58(1 Suppl):ONS-E177.

Buvanendran A, et al. 2008. Efficacy of transverse tripolar spinal cord stimulator for the relief of chronic low back pain from failed back surgery. Pain Physician. 11(3):333-338.

Frey ME, et al. 2009. Spinal cord stimulation for patients with failed back surgery syndrome: a systematic review. Pain Physician. 12(2):379-397.

Hoppenstein R. 1975. Percutaneous implantation of chronic spinal cord electrodes for control of intractable pain: preliminary report. Surg Neurol. 4(1):195-198.

Johnson MR, et al. 2004. Minimally invasive implantation of epidural spinal cord neurostimulator electrodes by using a tubular retractor system. Technical note. J Neurosurg. 100(6):1119-1121.

Kumar K, et al. 1998. Epidural spinal cord stimulation for treatment of chronic pain—some predictors of success. A 15-year experience. Surg Neurol. 50(2):110-120.

Kumar K, et al. 2006. Spinal cord stimulation in treatment of chronic benign pain: challenges in treatment planning and present status, a 22-year experience. Neurosurgery. 58(3):481-496.

Kumar K, et al. 1991. Treatment of chronic pain by epidural spinal cord stimulation: a 10-year experience. J Neurosurg. 75(3):402-407.

North RB, et al. 1977-1978. Chronic dorsal column stimulation via percutaneously inserted epidural electrodes. Preliminary results in 31 patients. Appl Neurophysiol. 40(2-4):184-191.

North RB, et al. 1977. Chronic stimulation via percutaneously inserted epidural electrodes. Neurosurgery. 1(2):215-218.

North RB, et al. 2002. Spinal cord stimulation electrode design: prospective, randomized, controlled trial comparing percutaneous and laminectomy electrodes. Part I: technical outcomes. Neurosurgery. 51(2):381-389.

North RB, et al. 2005. Spinal cord stimulation for axial low back pain: a prospective, controlled trial comparing dual with single percutaneous electrodes. Spine (Phila Pa 1976). 30(12):1412-1418.

North RB, et al. 1993. Spinal cord stimulation for chronic, intractable pain: experience over two decades. Neurosurgery. 32(3):384-394.

North RB, et al. 2005. Spinal cord stimulation versus repeated lumbosacral spine surgery for chronic pain: a randomized, controlled trial. Neurosurgery. 56(1):98-106.

North RB. 1993. Spinal cord stimulation for chronic, intractable pain. Adv Neurol. 63:289-301.

Urban BJ, et al. 1978. Percutaneous epidural stimulation of the spinal cord for relief of pain. Long-term results. J Neurosurg. 48(3):323-328.

Wilkinson HA. 2008. Spinal cord stimulation versus reoperation for failed back surgery syndrome: a cost effectiveness and cost utility analysis based on a randomized, controlled trial. Neurosurgery. 63(2):E376.

* cited by examiner

SPINAL CORD STIMULATION SYSTEM AND METHODS OF USING SAME

CROSS-REFERENCE TO RELATED APPLICATIONS

This application claims priority to U.S. Provisional Application No. 61/368,501, filed on Jul. 28, 2010, and to U.S. Provisional Application No. 61/415,181, filed on Nov. 18, 2010, the disclosures of which are hereby incorporated herein by reference in their entirety.

FIELD OF THE INVENTION

This invention relates to a spinal cord stimulation method and, more particularly, to systems and methods for optimizing the stimulation of the dorsal column of the spinal cord.

BACKGROUND

Dorsal column stimulation is an established technology for management of chronic low back and leg pain when other surgical options have failed or are not feasible. Conventional dorsal column stimulation systems treat chronic pain by providing electrical stimulation pulses through an electrode array placed in the epidural space next to a patient's spinal cord. The stimulation parameter set determines the characteristics of the stimulation pulses provided through the electrode array in conjunction with the electrodes used to provide the stimulation pulses. Typically, the optimal stimulation parameter set for a specific patient can be determined from the response of the patient to various sets of stimulation parameters.

A dorsal column stimulation system typically includes an implantable pulse generator (IPG), an electrode array, an electrode lead, and an electrode lead extension. Conventionally, the electrodes are implanted against the outer surface of the dura, which is a membrane that surrounds the spinal cord. In operation, the IPG generates electrical pulses that are delivered, via the implanted electrodes, to the dorsal column and dorsal root fibers within the spinal cord. In one aspect, the electrodes are typically arranged and spaced in a desired pattern to create an electrode array and individual wires within one or more electrode leads are connected with each electrode in the array. The electrode leads exit the spinal column and can be attached to one or more electrode lead extensions, which, in turn, are typically tunneled subcutaneously around the torso of the patient to a subcutaneous pocket where the IPG is implanted.

In order for dorsal column stimulation to be effective, the electrodes should be placed in a location such that the electrical stimulation will affect the targeted nerves and cause paresthesia (a feeling of tingling or numbness). The paresthesia perceived by the patient and induced by the stimulation should ideally be located in approximately the same place in the patient's body as the pain that is the target of treatment. If one or more electrodes in the electrode array are not correctly positioned, it is possible that the patient will receive little or no benefit from an implanted dorsal column stimulation system. Thus, correct electrode placement can mean the difference between effective and ineffective pain therapy.

However, precise placement of an electrode relative to the patient's distribution of pain can be difficult due to anatomic variations among patients and due to the inherent limitations of standard electrode designs. Conventionally, electrodes are made of flexible plastic and are inserted into the epidural space through an opening created by a laminotomy procedure that involves the removal of the posterior aspect of a vertebra, which normally forms the spinal canal and protects the spinal cord. Typically, because the electrode is pushed into position by its tail, the electrode will generally follow the path of least resistance, which often results in suboptimal or undesired placement of the electrode with respect to the stimulation target. It is also known that the patient's anatomy can cause deflection of the electrode during the electrode insertion process, thereby making midline electrode placement difficult to achieve. Even a perfect midline placement, as judged by flouroscopy, can result in unilateral stimulation rather than bilateral stimulation of the spinal cord. This problem can prevent optimal electrode placement and, consequently, limit the pain relief experienced by the patient.

There are several known options for overcoming the problems associated with electrode placement; however, each option has significant limitations. One conventional option is the use of a percutaneous cylindrical electrode. These electrodes are typically introduced through a needle and have an internal (coaxial) guidewire that can be contoured to assist with accurate placement. While percutaneous electrodes are well suited for ambulatory trial purposes, these electrodes are not reliable for long-term uses. Specifically, the round, thin designs of percutaneous electrodes make them vulnerable to migration and pullout. Additionally, percutaneous electrodes have compact electrode contact arrays that limit their stimulation distribution. Further, percutaneous electrodes rapidly consume their batteries as energy is expended radially from the electrode contacts rather being exclusively directed toward the spinal cord.

Another conventional option for overcoming the problems associated with electrode placement is the use of paddle-style electrodes, which cover a larger surface area and have an extensive contact array that allows for flexibility with programming stimulation parameters. Paddle-style electrodes are also likely to be relatively stable once post-operative scarring occurs. However, it is difficult to adjust the positioning of paddle-style electrodes without more extensive surgical procedures. Conventionally, an extensive laminectomy can be used to expose the entire site for planned electrode coverage. This requires a larger incision and more muscle manipulation that can add time and morbidity to the procedure. Alternatively, a separate laminotomy superior to a first laminotomy can be utilized (either through the same or a second incision) to visualize and adjust the electrode. This too requires a larger incision and muscle manipulation.

Accordingly, there is a need in the pertinent art for systems and methods of dorsal column stimulation that allow for precise, efficient, and stable placement and repositioning of stimulating electrodes while requiring only a single small incision. There is a further need for systems and methods of dorsal column stimulation that allow for precise, efficient, and stable placement and repositioning of stimulating electrodes through restriction of the contouring of the stimulating electrodes during implantation. There is a further need for systems and methods of dorsal column stimulation that allow for precise, efficient, and stable placement and repositioning of stimulating electrodes using through the use of stimulating electrodes that are configured to promote the formation of a desired insertion pathway within the body of the subject.

SUMMARY

Described herein are methods for optimizing stimulation of the dorsal column of the spinal cord of a subject. The method includes providing a stimulating electrode array and a frame element. In one aspect, the stimulating electrode array has an engagement portion and a peripheral side edge and comprises electrodes. In another aspect, the frame element conforms to a portion of the peripheral side edge of the stimulating electrode array. In an additional aspect, the frame element is formed from a material that is more rigid than the stimulating electrode array. In a further aspect, the method includes selectively coupling the frame element thereto the engagement portion of the stimulating electrode array. In still a further aspect, the method includes inserting the coupled frame element and stimulating electrode array into the body of the subject at a desired position proximate the dorsal column of the subject. In still a further aspect, the method includes disengaging the frame element from the engagement portion of the stimulating electrode array such that the stimulating electrode array remains in the desired position.

In exemplary aspects, the stimulating electrode array can be inserted into the body of the subject with the assistance of a steering member having a handle, a housing, and a snare means. In these exemplary aspects, the snare means is positioned within the housing and is selectively extendable and retractable relative to an opening in a distal end of the housing. In a further aspect, the snare means is configured to engage at least a portion of the engagement portion of the stimulating electrode array.

Systems of optimizing stimulation of the dorsal column of the spinal cord of a subject are also described herein.

BRIEF DESCRIPTION OF THE FIGURES

These and other features of the preferred embodiments of the invention will become more apparent in the detailed description in which reference is made to the appended drawings wherein:

FIG. 3 is an image depicting a close-up view of the engagement between the snare means of the steering member and the engagement portion of the stimulating electrode array. FIG. 4 is an image depicting an expanded view of the engagement between the snare means of the steering member and the engagement portion of the stimulating electrode array.

As shown in FIG. 5, the handle can include a thumb guide ring for activation of the snare means as described herein.

FIG. 6 is an image depicting a top close-up view of the engagement between the snare means of the two steering members and the corresponding engagement portions of the stimulating electrode array. FIG. 7 is an image depicting an expanded view of the engagement between the snare means of the two steering members and the corresponding engagement portions of the stimulating electrode array. FIG. 8 is an image depicting another top close-up view of the engagement between the snare means of the two steering members and the corresponding engagement portions of the stimulating electrode array.

DETAILED DESCRIPTION

Figure 1:
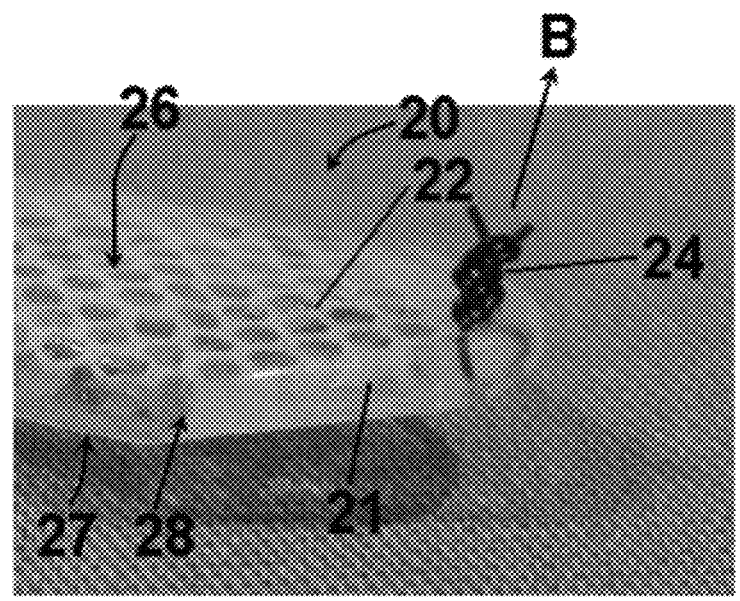
FIG. 1 is an image of an engagement portion of an exemplary stimulating electrode array as described herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a stimulating electrode" can include two or more such stimulating electrodes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

In one embodiment, and with reference to FIGS. 1-10, the invention relates to a system 10 for optimizing stimulation of the dorsal column of the spinal cord of the body of a subject. In one aspect, the system 10 comprises a stimulating electrode array 20 comprising a plurality of electrodes 22. In this aspect, the stimulating electrode array 20 can be a paddle-style electrode array as is conventionally known in the art, such as, for example and without limitation, a two-column octet electrode array (Boston Scientific) and a three-column 5-6-5 electrode array (Medtronic). It is contemplated that the plurality of electrodes 22 can comprise any number of electrodes, including, for example and without limitation, 1, 2, 3, 4, 5, 6, 7, 8, 9, 10, 11, 12, 13, 14, 15, 16, 17, and 18 electrodes. In one aspect, the stimulating electrode array has a longitudinal axis.

In another aspect, the stimulating electrode array 20 can comprise at least one lead 25. It is contemplated that each lead 25 of the at least one lead can comprise a conventional lead, including, for example and without limitation, conventional electrical wiring. In an additional aspect, each respective at least one lead 25 can be placed in electrical communication with a respective paired at least one electrode 22 of the electrode array 20. Optionally, and as exemplarily depicted in FIG. 5, the system 10 can comprise a holder 70 for stabilizing the orientation of the stimulating electrode array 20, including the leads 25, during implantation.

It is contemplated that each lead can be operably coupled in electrical communication with an Implantable Pulse Generator (IPG) or other conventional means for creating electrical pulses, thereby permitting electrical transmission of pulses coupled to the at least one electrode 22 of the stimulating electrode array 20. It is further contemplated that the IPG or other means for creating electrical pulses can be selectively programmable to stimulate the at least one lead and the electrically coupled at least one electrode 22 in a desired pattern and sequence. It is still further contemplated that the IPG or other means for creating electrical pulses can be selectively programmed through the skin of the subject following implantation.

In an additional aspect, as shown in FIG. 1, the stimulating electrode array 20 can have a top surface 26, a bottom surface 27, and a peripheral side edge 28. In a further aspect, the stimulating electrode array 20 has at least one engagement portion 24. In this aspect, each engagement portion 24 is configured for engagement with a surgical tool. It is contemplated that each engagement portion 24 can be, for example and without limitation, a suture knot, a hook, a loop, or other protrusion that is configured for engagement with a surgical tool. It is further contemplated that each engagement portion 24 can be prepared as desired by a surgeon prior to implantation of the stimulating electrode array. Alternatively, the stimulating electrode array 20 can be manufactured with the at least one engagement portion 24 such that the surgeon is not required to prepare the engagement portions. One skilled in the art will appreciate that it is understood that any conventional means for engagement with a conventional surgical tool are contemplated as being within the scope of this disclosure.

In one exemplary aspect, the at least one engagement portion 24 can be positioned proximate a distal portion 21 of the stimulating electrode array 20. In another exemplary aspect, the at least one engagement portion 24 can be positioned proximate a medial portion 23 of the stimulating electrode array 20. In further exemplary aspects, the at least one engagement portion 24 can be positioned at one or more selected locations along the peripheral side edge 28 of the stimulating electrode array 20. Alternatively, it is contemplated that the at least one engagement portion 24 can be positioned on the top surface 26 of the stimulating electrode array 20. However, it is contemplated that the at least one engagement portion 24 can be positioned in any location thereon the stimulating electrode array 20 that is accessible by a medical practitioner, as described herein.

Optionally, in an additional aspect, the system 10 can comprise at least one steering member 40. In this aspect, each steering member 40 can have a longitudinal axis A. In one aspect, each steering member 40 of the at least one steering member can comprise an elongate housing 42. In this aspect, the housing 42 can have a distal end 44 that defines an opening 46. In one aspect, the distal end 44 of the housing 42 can comprise a blunt or dulled tip. Optionally, the housing 42 can be inwardly tapered proximate its distal end 44 relative to the longitudinal axis A of the steering member 40. In an exemplary aspect, the steering member 40 can have a longitudinal length ranging from about 12 inches to about 18 inches.

In one aspect, the housing 42 of each steering member 40 of the at least one steering member can comprise conventional, sterilizable, surgical instrument materials. In a further aspect, it is contemplated that the housing 42 can comprise one or more materials that are conventionally used to produce medical implants and surgical instruments, including, for example and without limitation, metal and polymeric materials. In one aspect, at least portions of the housing 42 can comprise a metal that is radio-opaque and, thus, visible through conventional fluoroscopic imaging procedures. For example, and without limitation, the housing 42 can comprise stainless steel. It is also contemplated that at least a portion of the housing 42 can comprise a radio-lucent material, such as, for example and without limitation, corrugated plastic. It is further contemplated that a radio-lucent housing can minimize visibility of the housing during conventional fluoroscopic imaging procedures. In another aspect, at least a portion of the housing 42 can be malleable. In this aspect, it is contemplated that the malleable housing can be readily and selectively contoured to a desired shape.

Figure 2:
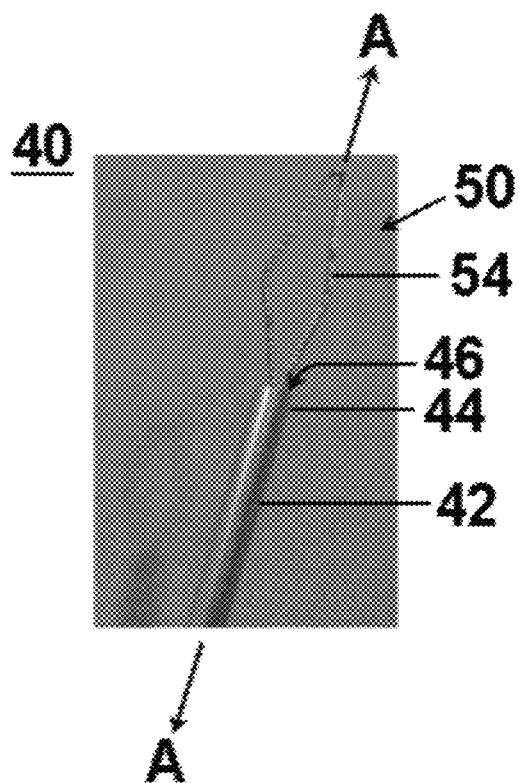
FIG. 2 is an image of the housing and snare means of an exemplary steering member as described herein.

In a further aspect, as shown in FIG. 2, each steering member 40 of the at least one steering member can comprise a snare means 50 positioned within the housing 42 that is configured to be movable about and between an extended position and a retracted position relative to the opening 46 of the housing along the longitudinal axis A of the steering member. In this aspect, it is contemplated that, in the extended position, the snare means can extend from the distal end 44 of the housing 42 by a distance ranging from about 3 mm to about 7 mm and more preferably being about 5 mm. In one aspect, the snare means 50 can comprise an elongate member positioned within the housing 42 of the steering member 40, wherein a retractable portion 54 of the elongate member can be moved about and between the extended position and the retracted position relative to the opening 46 of the housing. In this aspect, the elongate member can comprise, for example and without limitation, a wire, a cable or other flexible material that possesses sufficient strength to function as described herein.

Figure 3:
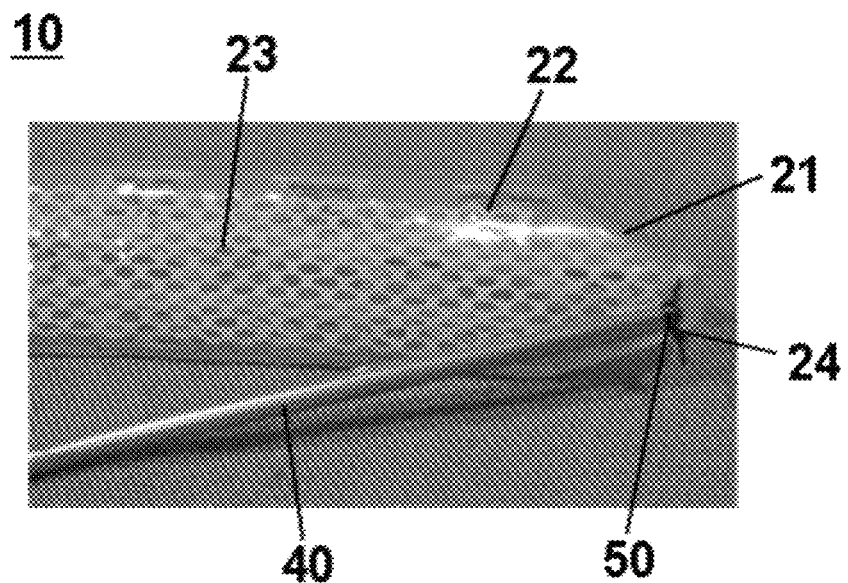
FIGS. 3-4 are images of an exemplary engagement between the snare means of FIG. 2 and the engagement portion of FIG. 1 as described herein.
Figure 4:
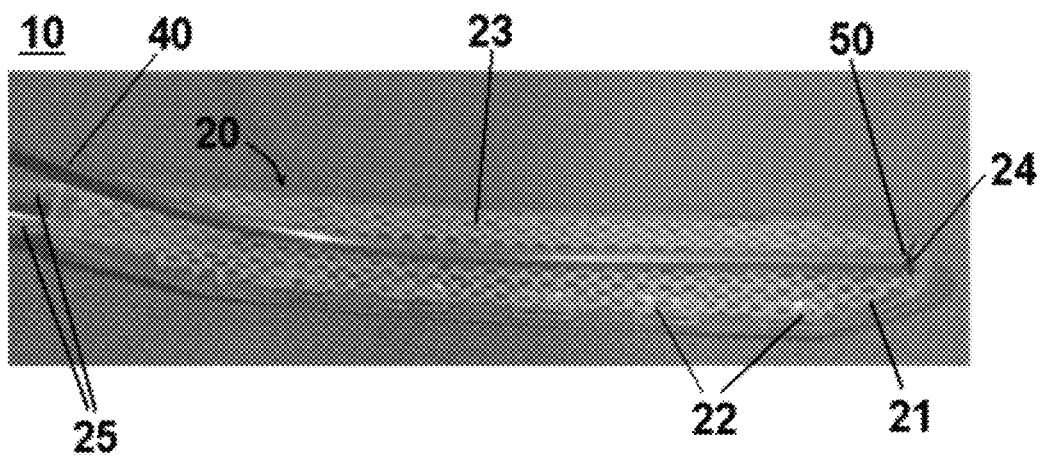

In an additional aspect, as depicted in FIGS. 3-4, the snare means 50 can be configured to operatively engage at least a portion of an engagement portion 24 of the at least one engagement portion of the stimulating electrode array 20. It is contemplated that the snare means 50 can comprise a loop, a hook, a threaded shape, or any conventional shape that can be configured to engage an engagement portion 24 of the stimulating electrode array 20. In one exemplary aspect, each engagement portion 24 of the stimulating electrode array 20 can comprise a guide loop configured to receive the snare means 50 of a corresponding steering member 40. It is contemplated that combinations of different types of engagement portions can be used within the scope of this disclosure. For example, in an exemplary aspect, it is contemplated that a guide loop can be positioned thereon the medial portion 23 of the stimulating electrode array 20 and another engagement portion 24 can be positioned thereon the distal portion 21 of the stimulating electrode array. In this aspect, it is contemplated that the guide loop and the engagement portion can be axially aligned such that a steering member can be passed through the guide loop and then used to engage the engagement portion on the distal portion of the stimulating electrode array.

Figure 10:
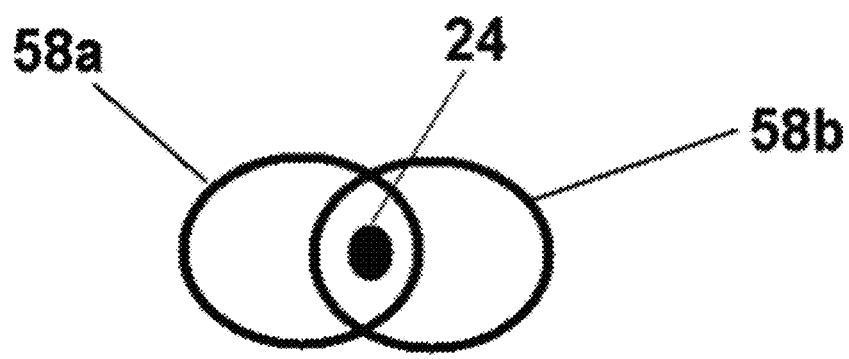
FIG. 10 is a front perspective view of an exemplary snare means including first and second loops, as described herein.

In another aspect, as depicted in FIG. 10, the snare means 50 can comprise a first loop 58a and a second loop 58b. In this aspect, each engagement portion 24 of the stimulating electrode array 20 can have a longitudinal axis B and can protrude therefrom the stimulating electrode array. It is contemplated that both the first and second loops 58a, 58b of the snare means 50 can be configured to receive an engagement portion 24 of the stimulating electrode array 20. It is further contemplated that, following receipt of the engagement portion 24 within both the first loop 58a and the second loop 58b of the snare means 50, the steering member 40 can be configured to retract the snare means such that the first loop and the second loop of the snare means are pulled in opposing directions relative to the longitudinal axis B of the engagement portion, thereby engaging the engagement portion of the stimulating electrode array 20.

Figure 5:
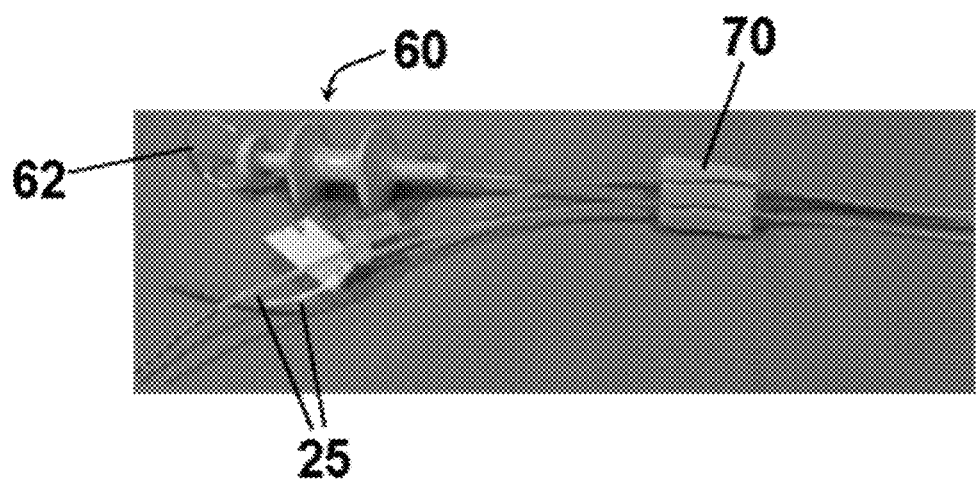
FIG. 5 is an image of the handle of an exemplary steering member as described herein.

In an additional aspect, and with reference to FIG. 5, each steering member 40 of the at least one steering member can comprise a handle 60. It is contemplated that the snare means 50 can be coupled to the handle 60 of a steering member 40, and the handle can comprise means for selectively deploying and retracting the snare means such that an engagement portion 24 of the stimulating electrode array 20 is engaged. In an exemplary aspect, the handle 60 can comprise a thumb guide ring 62 that is operatively coupled to the snare means. In another exemplary aspect, it is contemplated that the handle 60 can comprise, for example and without limitation, a conventional spring-loaded plunger mechanism that is moveable axially along the longitudinal axis A of the steering member 40 and is configured to effect movement of the snare means 50 about and between the extended position and the retracted position. In an additional exemplary aspect, it is contemplated that the steering member 40 can be a conventional suture retrieval snare, such as, for example and without limitation, those manufactured by Smith & Nephew, Inc. (Andover, Mass.). It is further contemplated that the operation and design of the steering member 40 can be substantially the same as the suture snares described in U.S. Pat. Nos. 4,779,616, 5,501,692, 5,921,918, the disclosures of which are incorporated by reference in their entirety. It is contemplated that the operative coupling between the snare means 50 and the handle 60 as described herein can permit selective, one-handed activation by a user, such as a surgeon. In one aspect, when the distal end 44 of the housing 42 of a steering member 40 has a blunt tip, it is contemplated that, during movement of the steering member while the snare means 50 of the steering member is positioned in the retracted position, the blunt tip of the housing can be configured to prevent the steering member from engaging and becoming entangled with soft tissue of the epidural space of a subject.

In one aspect, it is contemplated that, following engagement between the snare means 50 and an engagement portion 24 of the stimulating electrode array 20, the snare means can be configured to selectively retain the engagement portion of the stimulating electrode array proximate to, or against, the distal end 44 of the housing 42 of a steering member 40. In this aspect, it is contemplated that, when the snare means 50 is retracted toward the housing 42, the engagement portion 24 will remain engaged with the snare means such that the engagement portion is retained proximate to, or abuts, the distal end 44 of the housing. In still a further aspect, a steering member 40 of the at least one steering member can be configured to permit a surgeon to guide the stimulating electrode array 20 to a desired position proximate the dorsal column of the spinal cord of the subject. Optionally, upon positioning of the stimulating electrode array 20 at the desired position, the snare means 50 of a steering member 40 can be configured to release or otherwise disengage the engagement portion 24 of the stimulating electrode array such that the stimulating electrode array remains in the desired position.

Figure 14:
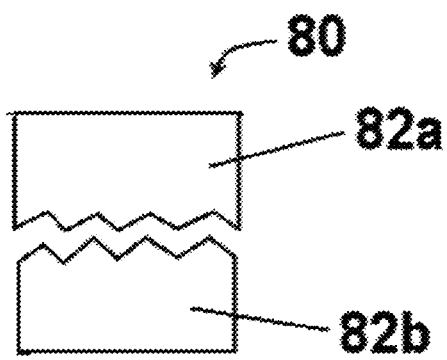
FIG. 14 is a close-up view of an exemplary jaw assembly as described herein.

Alternatively, in an optional aspect, and with reference to FIG. 14, rather than having a snare means 50 for engaging the at least one engagement portion 24 of the stimulating electrode array 20, a steering member 40 of the at least one steering member can comprise a jaw assembly 80 having two opposed jaw elements 82a, 82b. In this aspect, the opposed jaw elements 82a, 82b can be configured to be movable about and between an open position and a closed position. It is contemplated that, in the closed position, the opposed jaw elements 82a, 82b can close such that an engagement portion 24, such as, for example and without limitation, a conventional 3-0 suture, can be grasped without any slippage. It is contemplated that the opposed jaw elements 82a, 82b can be positioned outside of the housing 42 of a steering member 40 proximate the distal end 44 of the housing. In one aspect, the handle 60 of the steering member 40 can comprise means for selectively opening and closing the jaw assembly 80. For example, it is contemplated that the means for selectively opening and closing the jaw assembly can comprise an elongate member positioned within the housing 42 and operatively coupled to the opposed jaw elements 82a, 82b such that selective movement of the elongate member corresponds to opening and closing of the jaw assembly 80. It is further contemplated that the elongate member can be positioned in operative communication with a grip portion of the handle 60 of the steering member 40 such that a user can manipulate the handle using the grip portion to create axial movement of the elongate member along the longitudinal axis A of the steering member, thereby providing selective control of the opening and closing of the jaw assembly 80. In this aspect, the elongate member can comprise, for example and without limitation, a wire, a cable or other flexible material that possesses sufficient strength to function as described herein. It is contemplated that the operative coupling between the jaw assembly 80 and the handle 60 as described herein can permit selective, one-handed activation by a user, such as a surgeon. In a further aspect, the jaw elements 82a, 82b of the jaw assembly 80 can be spring-loaded.

In an additional aspect, the jaw assembly 80 can be configured to operatively engage at least a portion of the stimulating electrode array 20, such as, for example and without limitation, a portion of the top surface 26, the bottom surface 27, or the peripheral side edge 28 of the stimulating electrode array. Optionally, the jaw assembly 80 can be configured to operatively engage an engagement portion 24 of the at least one engagement portion of the stimulating electrode array 20.

Figure 9:
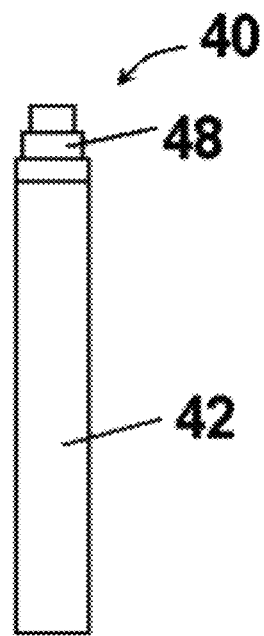
FIG. 9 is a perspective view of an exemplary steering member having a telescoping portion as described herein.

In another optional aspect, and as shown in FIG. 9, the distal end 44 of the housing 42 of the steering member 40 can have a telescoping portion 48 that is extendable and retractable along the longitudinal axis A of the steering member. In this aspect, the steering member 40 can comprise means for extending and retracting the telescoping portion 48. In one aspect, it is contemplated that the means for extending and retracting the telescoping portion 48 can comprise an elongate member, such as, for example and without limitation, a cable or a wire, that is operatively coupled to the telescoping portion 48. In this aspect, the elongate member can be in operative communication with the handle 60 of the steering member 40 such that a user can manipulate the handle to create axial movement of the elongate member along the longitudinal axis A of the steering member 40, thereby providing selective control of the extension and retraction of the telescoping portion 48 of the steering member. It is contemplated that, following engagement between the steering member 40 and the stimulating electrode array 20, the telescoping portion 48 of the steering member can be used to more effectively direct the stimulating electrode array to a desired position above an opening created during a laminotomy procedure.

In a further aspect, it is contemplated that a steering member 40 of the at least one steering member can be used to pull the stimulating electrode array 20 into position, thereby avoiding the tendency of flexible electrodes to follow the path of least resistance as they are conventionally pushed into place by their tails. It is further contemplated that the steering member 40 can be shaped and sized such that the steering member does not cause undesired dural stimulation during positioning of the stimulating electrode array 20. In yet another aspect, it is contemplated that the malleable steering member 40 can be contoured or otherwise shaped to accommodate a deep wound and/or to guide the stimulating electrode array 20 from a first position to a second position lateral or cephalad (more superior) to the first position. In this aspect, it is further contemplated that the malleable steering member 40 can have sufficient mechanical strength to permit a surgeon to accurately control movement of the steering member in any direction within the epidural space regardless of operational conditions.

In still a further aspect, it is contemplated that the cross-sectional dimensions of the housing 42 of a steering member 40 of the at least one steering member 40 can be reduced or flattened proximate the distal end 44 of the housing. For example, in one aspect, the housing 42 of the steering member 40 can have a cross-sectional diameter ranging from about 1 mm to about 3 mm. In this aspect, it is contemplated that the cross-sectional diameter of the housing 42 can be reduced proximate the distal end 44 of the housing. It is contemplated that reductions in the cross-sectional profile of the distal portions of the housing 42 can decrease the portion of the spinal canal that is occupied by the steering member 40 during positioning of the stimulating electrode array 20, as described herein. It is further contemplated that the resulting increase in unoccupied space within the spinal canal can facilitate epidural dissection.

Figure 6:
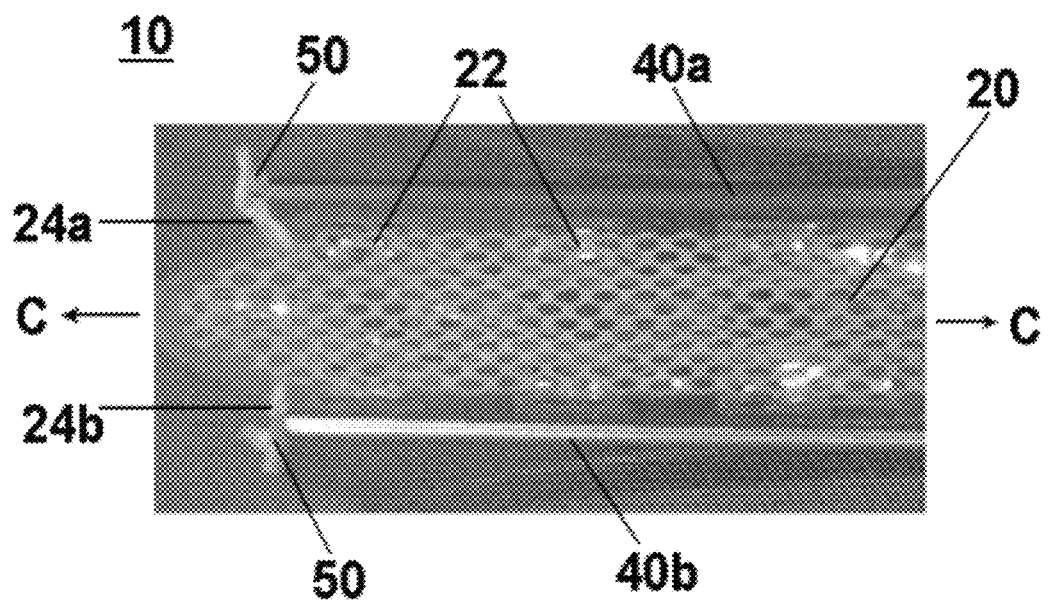
FIGS. 6-8 are images of an exemplary engagement between the snare means of two steering members and the corresponding engagement portions of a stimulating electrode array as described herein.
Figure 7:
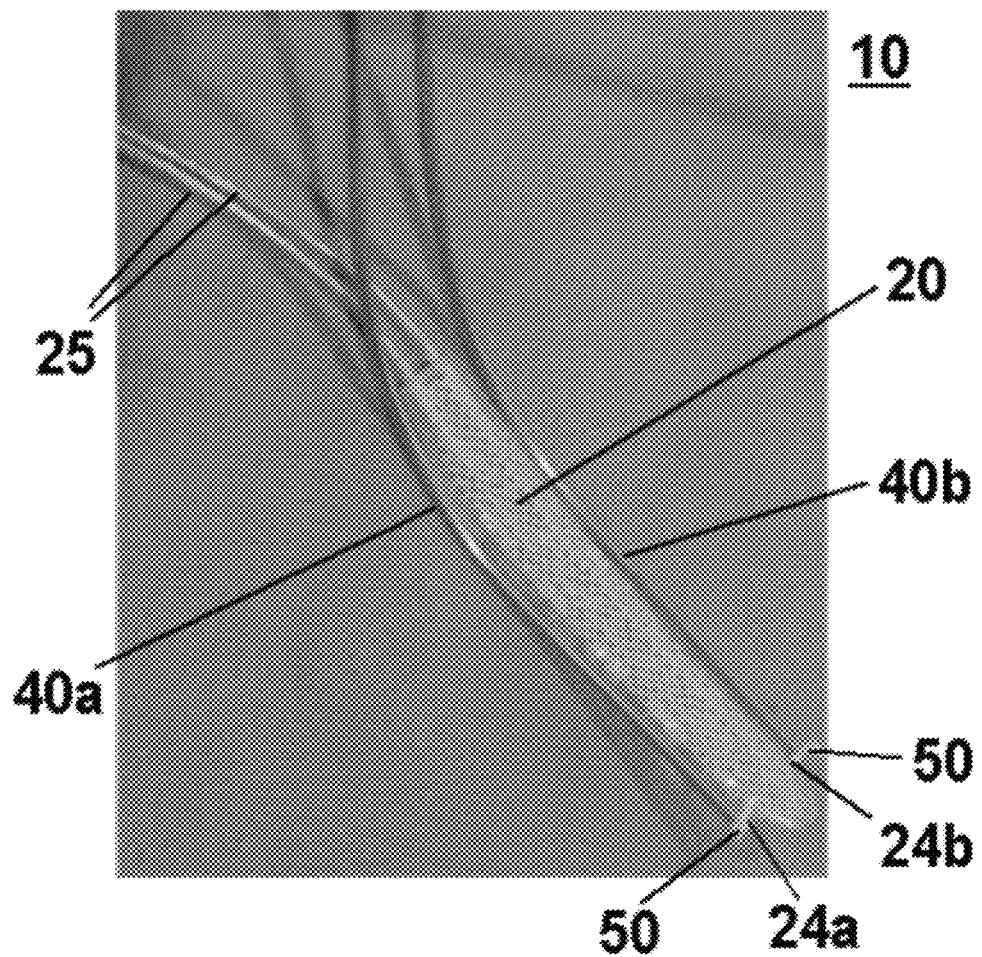
Figure 8:
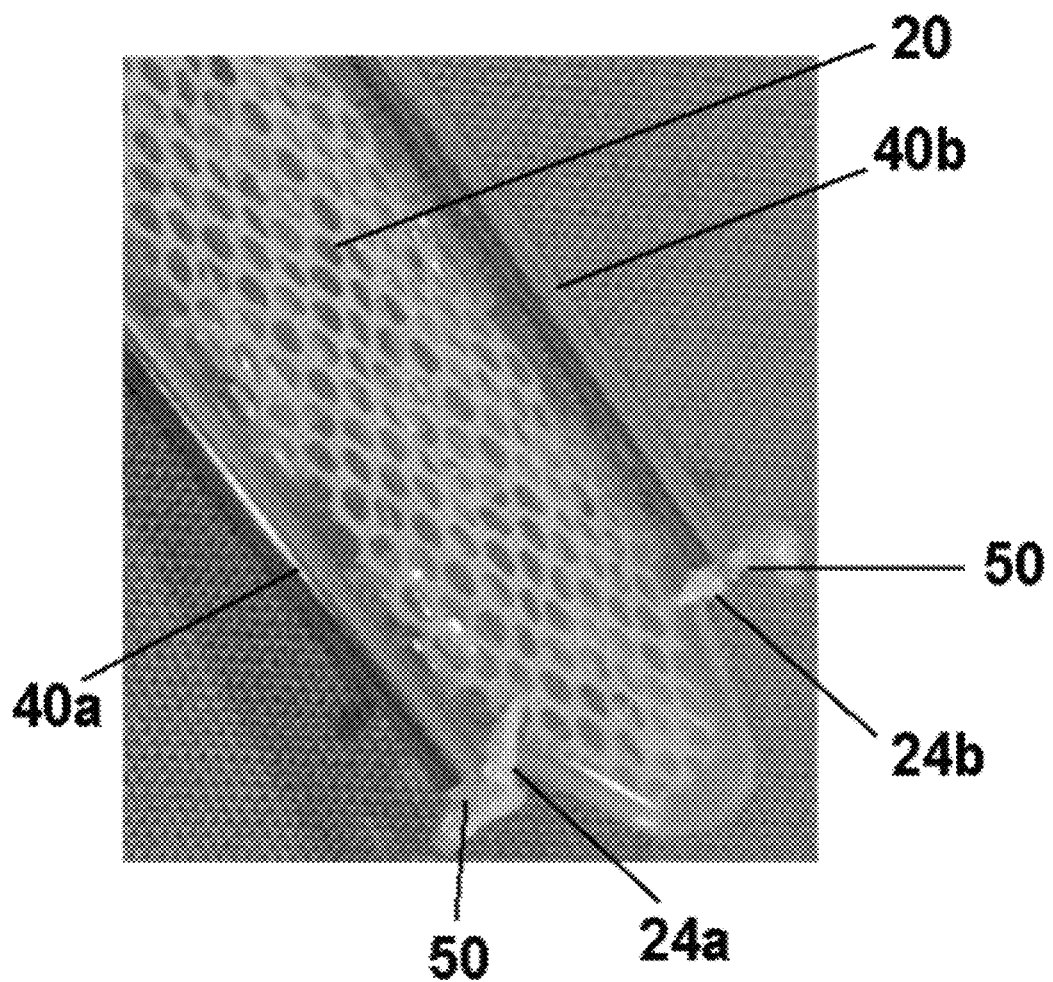

In one aspect, and as shown in FIGS. 6-8, the at least one engagement portion 24 of the stimulating electrode array 20 can comprise two spaced engagement portions. In this aspect, it is contemplated that the stimulating electrode array 20 can have a first engagement portion 24a and a second engagement portion 24b spaced from the first engagement portion. It is contemplated that the first engagement portion 24a can be spaced from the second engagement portion 24b along a longitudinal axis C of the stimulating electrode array 20. It is further contemplated that, as shown in FIGS. 6-8, the first engagement portion 24a can be spaced from the second engagement portion 24b substantially perpendicularly to the longitudinal axis C of the stimulating electrode array.

In an exemplary aspect, it is contemplated that a first steering member 40a as described herein can be used to engage the first engagement portion 24a while a second steering member 40b as described herein can be used to engage the second engagement portion 24b. As further depicted in FIGS. 6-8, the first engagement portion 24a and the second engagement portion 24b can be positioned thereon selected portions of the peripheral side edge 28 of the stimulating electrode array 20. In an exemplary aspect, the first and second engagement portions 24a, 24b can be positioned thereon the peripheral side edge 28 of the stimulating electrode array 20 proximate the distal portion 21 of the stimulating electrode array. In one aspect, the snare means of the first steering member 40a can be configured to engage the first engagement portion 24a of the stimulating electrode array 20 and the snare means of the second steering member 40b can be configured to engage the second engagement portion 24b of the stimulating electrode array.

In another aspect, following engagement between the snare means of the first and second steering members 40a, 40b and the stimulating electrode array 20, when the snare means are retracted toward the housings of each respective steering member, the snare means of the first steering member 40a can be configured to selectively retain the first engagement portion 24a against the distal end of the housing of the first steering member and the snare means of the second steering member 40b can be configured to selectively retain the second engagement portion 24b against the distal end of the housing of the second steering member. In a further aspect, the first and second steering members 40a, 40b can be configured to cooperatively guide the stimulating electrode array 20 to a desired position proximate the dorsal column of the spinal cord of the subject. It is contemplated that the above-described placement of the first and second engagement portions 24a, 24b and the use of two steering members 40a, 40b can improve the accuracy with which the stimulating electrode array is positioned. It is further contemplated that the lateral placement of the first and second engagement portions 24a, 24b can decrease the thickness of the steering member-electrode array assembly during insertion within the spinal canal of the subject.

Alternatively, it is contemplated that a steering member 40 as described herein can comprise first and second snare means that are spaced along the longitudinal axis A of the steering member. In an exemplary aspect, the first engagement portion 24a can be positioned proximate the distal portion 21 of the stimulating electrode array 20 and the second engagement portion 24b can be positioned proximate the medial portion 23 of the stimulating electrode array 20, and the first snare means can be used to engage the first engagement portion while the second snare means can be used to engage the second engagement portion. Similarly, it is contemplated that a steering member 40 as described herein can comprise first and second jaw assemblies that are spaced along the longitudinal axis A of the steering member, and the first jaw assembly can be used to engage the first engagement portion 24a while the second jaw assembly can be used to engage the second engagement portion 24b. It is contemplated that the two spaced engagement portions 24a, 24b can permit more stable and/or parallel re-positioning of the stimulating electrode array than is provided by a single engagement portion.

Figure 11:
FIG. 11 is a side perspective view of the distal beveled portion of the peripheral side edge of an exemplary stimulating electrode array, as described herein.

Optionally, and with reference to FIG. 11, in another exemplary aspect, at least a portion of the peripheral side edge 28 of the stimulating electrode array 20 can comprise a substantially rigid biocompatible and biodegradable material, such as, for example and without limitation, a conventional biodegradable polymer. It is contemplated that the substantially rigid biodegradable material can be at least one of Poly(glycolide), Poly(glocolic acid-co-L-lactic acid), Poly(L-lactide), Poly(L-lactic acid-co-e-caprolactone), Poly(e-caprolactone), Poly(p-dioxanone), and Poly(orthoester). In this aspect, it is contemplated that the substantially rigid biodegradable material can be configured to degrade within the body of the subject at a predetermined rate. It is contemplated that, when the predetermined rate of degradation of the substantially rigid biodegradable material corresponds to the period of time required for complete degradation to occur, the rate of degradation of the substantially rigid biodegradable material can range from about 5 minutes to about 1 day, more preferably ranging from about 10 minutes to about 2 hours, and most preferably ranging from about 30 minutes to about 90 minutes. In an exemplary aspect, when the predetermined rate of degradation of the substantially rigid biodegradable material corresponds to the period of time required for complete degradation to occur, the rate of degradation of the substantially rigid biodegradable material can be about one hour. In another aspect, the substantially rigid biodegradable material can be a bioabsorbable material. In these aspects, it is contemplated that, upon implantation, the stimulating electrode array 20 can be suitably rigid to prevent undesired movement or contouring of the stimulating electrode array as the stimulating electrode array approaches a desired position proximate the dorsal column of the spinal cord of the subject. It is further contemplated that, following degradation of the substantially rigid biodegradable material, the stimulating electrode array 20 can be sufficiently flexible for desired positioning proximate the dorsal column of the spinal cord of the subject.

Optionally, in a further aspect, the peripheral side edge 28 of the stimulating electrode array 20 can comprise a distal beveled portion 29. In this aspect, it is contemplated that the distal beveled portion 29 of the stimulating electrode array can be configured to cut through tissue to thereby form an insertion pathway for passage of the stimulating electrode array. In an exemplary aspect, the portion of the peripheral side edge 28 that comprises the substantially rigid biodegradable material can include the distal beveled portion 29. In this aspect, it is contemplated that the distal beveled portion 29 of the peripheral side edge 28 can degrade within the body of the subject to thereby avoid undesired injury to the tissue of the patient.

Figure 12:
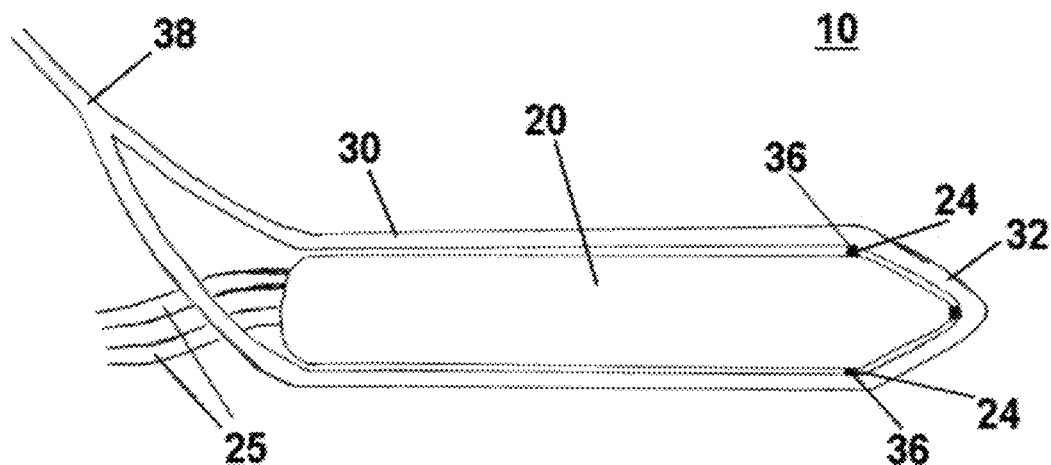
FIG. 12 is a perspective view of an exemplary frame element that is coupled to a stimulating electrode array, as described herein.
Figure 13:
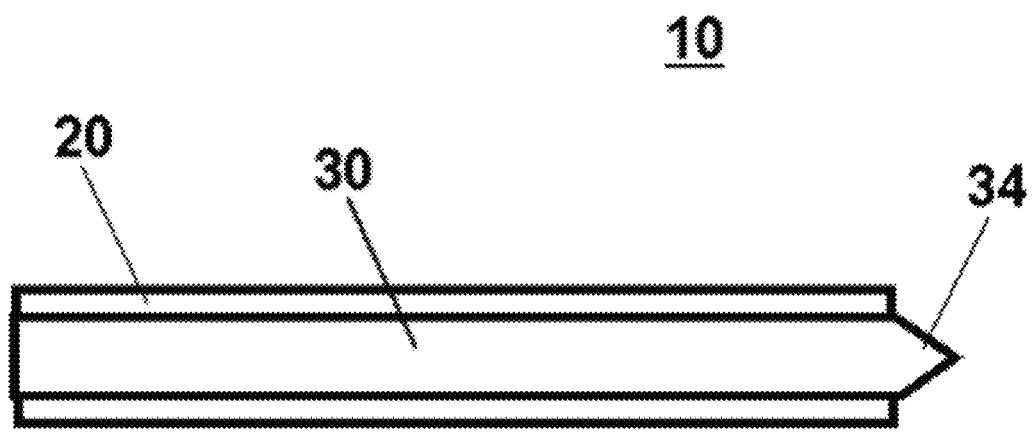
FIG. 13 is a side perspective view of the beveled edge of the frame element of FIG. 12.

Optionally, in a further aspect, and with reference to FIGS. 12-13, the system 10 can comprise a frame element 30 configured to conform to at least a portion of the peripheral side edge 28 of the stimulating electrode array 20. Optionally, the frame element 30 can be configured to conform to the peripheral side edge 28 of the stimulating electrode array within at least the distal portion 21 of the stimulating electrode array. In this aspect, the frame element 30 can comprise at least one snare means 36, such as described herein with respect to the steering member 40, for selectively coupling with a corresponding engagement portion 34 of the stimulating electrode array 20. It is contemplated that the selective coupling between the frame element 30 and the stimulating electrode array 20 can permit precise positioning of the stimulating electrode array within the body of the subject.

In another aspect, the frame element 30 can comprise a handle portion 38 configured to permit selective advancement of the coupled frame element 30 and stimulating electrode array 20 within the body of the subject. In a further aspect, the handle portion 38 of the frame element 30 can comprise means for selectively deploying the snare means 36 of the frame element such that the snare means engages a corresponding engagement portion 24 of the stimulating electrode array 20. It is contemplated that the means for selectively deploying the snare means 36 of the frame element 30 can substantially correspond to the means for selectively deploying the snare means 50 of the steering member 40, as described herein. For example, it is contemplated that the handle portion 38 of the frame element 30 can be in operative communication with an elongate element, such as, for example and without limitation, a conventional spring-loaded plunger mechanism or other elongate member, that is moveable within the frame element 30 and is configured to effect movement of the snare means 36 about and between an extended position and a retracted position. In an exemplary aspect, the handle portion 38 of the frame element 30 can have a thumb guide ring that is operatively coupled to the snare means 36.

Alternatively, in another optional aspect, rather than having a frame element 30 that is selectively coupled to the stimulating electrode array 20, the frame element 30 can be integrated into the stimulating electrode array 20. In this aspect, it is contemplated that the handle portion 38 of the frame element 30 can be selectively attachable to and detachable from the stimulating electrode array 20. In an exemplary aspect, the handle portion 38 can have a threaded portion that can be operatively received by a corresponding threaded portion defined therein the stimulating electrode array 30.

In another aspect, the frame element 30 can comprise a material that is more rigid than the stimulating electrode array 20 but also sufficiently malleable such that the frame element can be contoured to the shape of an insertion pathway formed by an epidural dissection tool. It is contemplated that the rigidity of the frame element can prevent undesired movement or contouring of the stimulating electrode array as the stimulating electrode array 20 approaches a desired position proximate the dorsal column of the spinal cord of the subject. In exemplary aspects, the frame element 30 can comprise one or more materials that are conventionally used to produce medical implants and surgical instruments, including, for example and without limitation, metal and polymeric materials, such as nitinol. In one aspect, at least portions of the frame element 30 can comprise a metal that is radio-opaque and, thus, visible through conventional fluoroscopic imaging procedures. It is also contemplated that at least a portion of the frame element 30 can comprise a radio-lucent material, such as, for example and without limitation, corrugated plastic. It is further contemplated that a radio-lucent frame element can minimize visibility of the housing during conventional fluoroscopic imaging procedures. In another aspect, at least a portion of the frame element 30 can be malleable. Optionally, the frame element 30 can have a substantially circular cross-section.

In an additional aspect, it is contemplated that the frame element 30 can comprise a distal portion 32 having a beveled edge 34. In this aspect, it is contemplated that the beveled edge 34 of the frame element 30 can be configured to cut through tissue to thereby form an insertion pathway for passage of the stimulating electrode array. In these aspects, it is contemplated that the frame element can effectively serve the purpose of both an epidural dissection tool and an electrode delivery/positioning tool.

In use, the systems described herein can be employed in a method for optimizing stimulation of the dorsal column of the spinal cord of a subject. It is contemplated that the method can be incorporated into a standard surgical procedure for accomplishing dorsal column stimulation. In one aspect, the surgical procedure can be a minimally invasive approach that only requires a single, small incision, thereby minimizing the recovery time and post-operative pain for the subject. In one aspect, the method can comprise the initial step of providing a stimulating electrode array as described herein. Optionally, in another aspect, the method can comprise providing at least one steering member as described herein. Alternatively, in another optional aspect, the method can comprise providing a frame element as described herein.

In an exemplary aspect, when the at least one steering member is provided, the method can comprise selectively deploying a snare means of the at least one steering member such that the snare means engages a corresponding engagement portion of the stimulating electrode array. Following the step of selectively deploying the snare means, the method can comprise selectively retracting the snare means such that the engagement portion of the stimulating electrode array is retained against the distal end of the housing. Following the step of selectively retracting the snare means, the method can comprise selectively moving the steering member such that the stimulating electrode array is guided to the desired position proximate the dorsal column of the spinal cord of the subject, as described herein. It is contemplated that the steps of selectively deploying the snare means and selectively retracting the snare means can be accomplished by selective operation of the handle of the steering member, as described herein. In another aspect, the method can further comprise releasing or otherwise disengaging the engagement portion of the stimulating electrode array from the snare means such that the stimulating electrode remains in the desired position. In a further aspect, the method can comprise the steps of removing the steering member, internalizing the stimulating electrode array and the IPG or other means for creating electrical pulses, and closing the surgical incision using conventional procedures.

In another exemplary aspect, when each steering member comprises a jaw assembly, the method can comprise selectively opening and closing the jaw assembly such that the jaw assembly engages a corresponding engagement portion of the stimulating electrode array. Following the step of selectively opening and closing the jaw assembly, the method can comprise selectively moving the steering member such that the stimulating electrode array is guided to the desired position proximate the dorsal column of the spinal cord of the subject, as described herein. It is contemplated that the steps of selectively opening and closing the jaw assembly can be accomplished by selective operation of the handle of the steering member, as described herein. In another aspect, the method can further comprise releasing or otherwise disengaging the engagement portion of the stimulating electrode array from the jaw assembly such that the stimulating electrode remains in the desired position. In a further aspect, the method can comprise the steps of removing the steering member, internalizing the stimulating electrode array and the IPG or other means for creating electrical pulses, and closing the surgical incision using conventional procedures.

In further aspects, when the distal end of the housing of each steering member has a telescoping portion, the methods can further comprise the step of selectively extending the telescoping portion following engagement between the steering member and the stimulating electrode array.

In an additional exemplary aspect, when a frame element is provided, the method can comprise selectively coupling the frame element thereto the at least one engagement portion of the stimulating electrode array as described herein. In a further aspect, the method can comprise inserting the coupled frame element and stimulating electrode array into the body of the subject at a desired position proximate the dorsal column of the subject. In another aspect, the method can comprise disengaging the frame element from the at least one engagement portion of the stimulating electrode array such that the stimulating electrode array remains in the desired position.

In one aspect, the step of inserting the coupled frame element and stimulating electrode array into the body of the subject can comprise selectively advancing a dissection tool configured to form an insertion pathway having a cross-sectional shape and size corresponding to a cross-sectional shape and size of the coupled frame element and stimulating electrode array.

In another aspect, when the frame element comprises a distal portion having a beveled edge, the step of inserting the coupled frame element and stimulating electrode array into the body of the subject can comprise selectively advancing the frame element to form an insertion pathway. It is contemplated that the insertion pathway formed by the frame element can be sized and shaped to receive the coupled frame element and stimulating electrode array and permit removal of the frame element without affecting the position of the stimulating electrode array.

In still another exemplary aspect, when a portion of the peripheral side edge of the stimulating electrode array comprises a rigid biodegradable material and has a distal beveled portion, the step of inserting the stimulating electrode array into the body of the subject can comprise selectively advancing the stimulating electrode array to form an insertion pathway. It is contemplated that the insertion pathway formed by the distal beveled portion of the stimulating electrode array can be sized and shaped to receive the stimulating electrode array.

It is contemplated that the step of selectively moving the steering member such that the stimulating electrode array is guided to the desired position can comprise monitoring the effectiveness of the stimulating electrode array at a variety of positions until the desired position is identified. In exemplary aspects, it is contemplated that the subject can be aroused from sedation while the stimulating electrode array is placed in an initial position, and the surgeon can conduct a stimulation trial, in which the subject can provide feedback as to the effectiveness of the stimulation that is applied by the stimulating electrode array in the initial position. Depending on the feedback from the subject, the position of the stimulating electrode array can be adjusted as necessary until a stimulation trial indicates that the stimulation provided by the stimulating electrode array at a particular location is satisfactory. It is contemplated that the location at which satisfactory stimulation occurs can correspond to the desired position of the stimulating electrode array. It is further contemplated that a steering member and/or frame element can remain engaged with the stimulating electrode array during trial stimulations such that the position of the stimulating electrode array can be quickly adjusted depending on the feedback received from the subject. Conventional imaging techniques, including fluoroscopy, can be used to confirm that the stimulating electrode array is maintained at the desired position.

Except where expressly stated to the contrary, it is contemplated that all elements of the systems disclosed herein can comprise biocompatible materials.

As one having ordinary skill in the art will appreciate, depending on the number of electrodes and the variety of stimulation pulses that can be generated within a system as described herein, the number of stimulation groups available presents numerous potential parameter sets that can be used by a surgeon or clinician. Accordingly, the methods described herein can further comprise selecting an effective stimulation parameter set for the subject. It is contemplated that the step of selecting an effective stimulation parameter set can comprise performing stimulation trials as described herein with different stimulation parameter sets until a satisfactory stimulation parameter set is identified.

EXAMPLES

A subject was placed prone on a radiolucent table and administered conventional sedation and antibiotics. A midline low thoracic incision was planned using surface landmarks and fluoroscopic guidance from an X-ray source. The surgical site was deeply infiltrated with local anesthetic, and a small incision was created over the T10 and T11 spinous processes. The dorsal fascia was incised and the paraspinous muscles were elevated sub-periosteally and retracted. The T10 spinous process was partially resected, and the trailing edge of the lamina was defined. Conventional bone rongeurs and curettes were then used to create a small laminotomy and expose the epidural space. The laminotomy was sized according to the widths of the electrodes of the stimulating electrode array to be implanted. A disposable curved epidural dissector or narrow malleable ribbon retractor was then used to create an initial epidural pathway by which the stimulating electrode array could be positioned within the epidural space.

The engagement portion of the stimulating electrode array was then prepared. As depicted in FIG. 1, a 3-0 vicryl suture was passed through the plastic at the distal end of the stimulating electrode array, just in front of the first electrode. The suture was passed from the dorsal surface of the electrode through to the ventral surface and then back through to the dorsal surface. Four knots were then tied, and the suture tails were trimmed. The knots served as the fixation point for the steering member. As shown in FIGS. 2-3, the snare means were then deployed and used to grasp the suture knot (the engagement portion). Once the snare means was retracted, the stimulating electrode array was securely attached to the steering member.

As depicted in FIG. 4, the steering member was then used to introduce the stimulating electrode array into the epidural space by pulling (rather than pushing) the electrode array into position. Gentle traction was applied on the lead wires while the steering member was advanced to allow the electrode array to be "shimmied" into position. Fluoroscopy was used to place the stimulating electrode array in the initial location. The subject was then aroused from sedation, and a subjective stimulation trial was conducted. The electrode was adjusted as necessary with fluoroscopic guidance. Once satisfactory stimulation coverage was achieved, the snare means was deployed to release the engagement portion (suture knot) of the stimulating electrode array, and the steering member was gently removed. A final image confirmed that the electrode array had not migrated. The subject was then re-sedated, and internalization of the IPG and leads proceeded in conventional fashion.

Figure 15A:
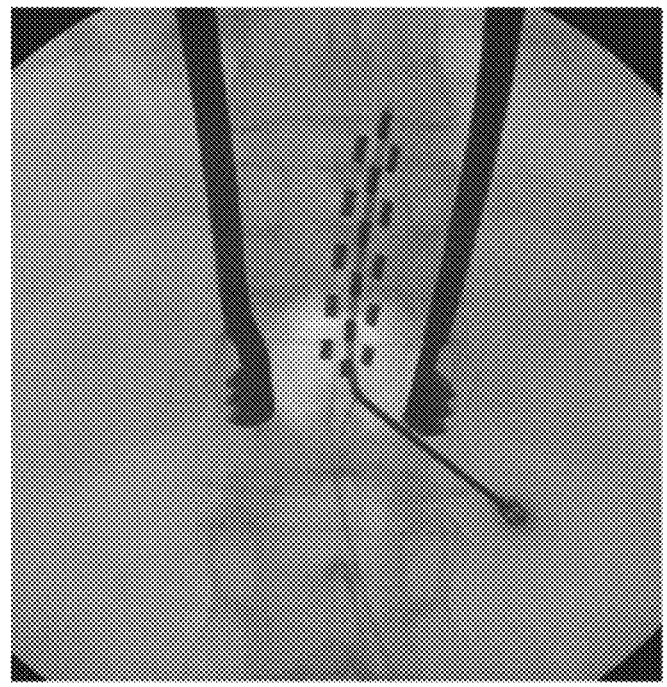
FIGS. 15A and 15B are intraoperative prone fluoroscopic images of an adjustment in the positioning of an exemplary stimulating electrode array as described herein from a right oblique location (FIG. 15A) to parallel left paramedian location (FIG. 15B).
Figure 15B:
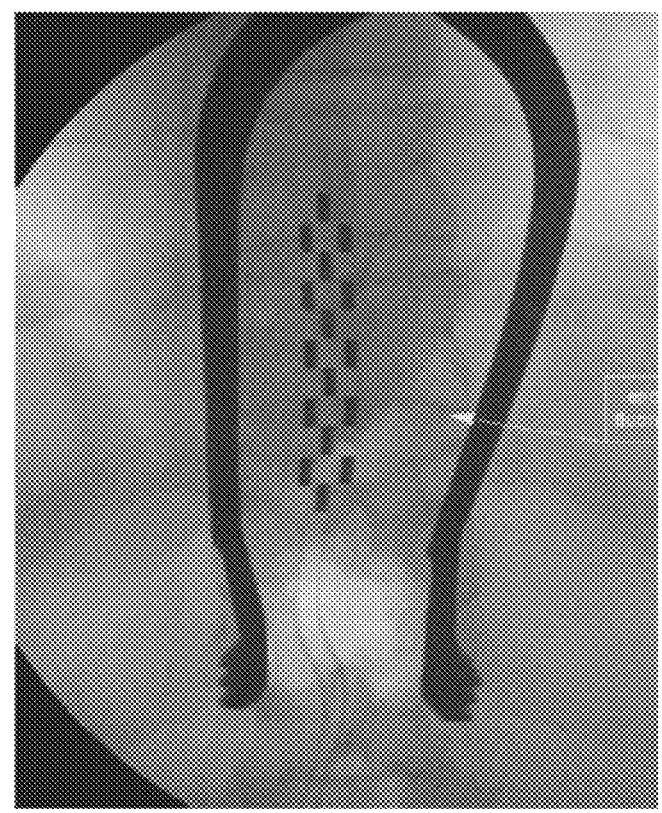

The described technique was used in patients during both initial electrode placement and in revision of previously placed epidural electrodes. Thirteen patients underwent first-time paddle-style electrode placement after a prior ambulatory trial with percutaneous electrodes. One patient underwent revision of a paddle-style electrode that had been placed several years earlier. In this patient, the epidural space was dissected with a malleable ribbon before placement of the new electrode. Another patient underwent placement of a paddle-style electrode after removal of percutaneous electrodes that had migrated. The time required for electrode placement was substantially reduced, generally being as short as 5 minutes and typically being less than 15 minutes. The intra-procedure discomfort for the patients, as judged subjectively by the patients, was also reduced. Stimulating electrode arrays as described herein were successfully and precisely positioned in both unilateral paramedian or midline positions. Paddle-style electrodes from different manufacturers have been placed, including a two-column octet electrode array (Boston Scientific) and three-column 5-6-5 electrode array (Medtronic). No procedural complications related to the methods described herein have been identified. Images of an exemplary adjustment in the positioning of a stimulating electrode array as described herein is depicted in FIGS. 15A and 15B.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for optimizing stimulation of the dorsal column of the spinal cord of the body of a subject, the method comprising:

removably coupling a frame element to a stimulating electrode array, the stimulating electrode array comprising a plurality of electrodes and having a top surface, a bottom surface, a peripheral side edge extending between the top surface and the bottom surface, and at least one engagement portion positioned along the peripheral side edge, the frame element configured to conform to at least a portion of the peripheral side edge of the stimulating electrode array, the frame element comprising a material that is more rigid than the stimulating electrode array, wherein the frame element is selectively removably coupled to the stimulating electrode array by the at least one engagement portion of the stimulating electrode array;

inserting the coupled frame element and stimulating electrode array into the body of the subject at a desired position proximate the dorsal column of the subject wherein the frame element comprises a distal portion having a beveled edge, and wherein the step of inserting the coupled frame element and stimulating electrode array into the body of the subject comprises selectively advancing the frame element to form an insertion pathway; and disengaging the frame element from the at least one engagement portion of the stimulating electrode array such that the stimulating electrode array remains in the desired position.

2. The method of claim 1, wherein the step of inserting the coupled frame element and stimulating electrode array into the body of the subject comprises selectively advancing a dissection tool configured to form an insertion pathway having a cross-sectional shape and size corresponding to a cross-sectional shape and size of the coupled frame element and stimulating electrode array.

3. The method of claim 1, wherein the frame element comprises nitinol.

4. A method for optimizing stimulation of the dorsal column of the spinal cord of the body of a subject, the method comprising:
  inserting a stimulating electrode array into the body of the subject proximate the dorsal column of the subject, the stimulating electrode array comprising a plurality of electrodes and having a top surface, a bottom surface, a peripheral side edge extending between the top surface and the bottom surface, and at least one engagement portion positioned along the peripheral side edge, the peripheral side edge having a distal beveled portion configured to cut through tissue of the subject to thereby form an insertion pathway, the distal beveled portion comprising a substantially rigid biodegradable material, the substantially rigid biodegradable material of the distal beveled portion configured to degrade within the body of the subject at a predetermined rate;
  inserting the stimulating electrode array into the body of the subject proximate the dorsal column of the subject, wherein the step of inserting the stimulating electrode array comprises forming an insertion pathway through the tissue of the subject using the distal beveled portion of the stimulating electrode array; and
  selectively moving the stimulating electrode array such that the stimulating electrode array is guided to a desired position proximate the dorsal column of the spinal cord of the subject,
  wherein, prior to degradation of the substantially rigid biodegradable material of the distal beveled portion, the stimulating electrode array is sufficiently rigid to prevent undesired movement of the stimulating electrode array during insertion of the stimulating electrode array, and wherein, following degradation of the substantially rigid biodegradable material of the distal beveled portion, the stimulating electrode array is sufficiently flexible for placement in the desired position.

5. The method of claim 4, wherein the step of inserting the stimulating electrode array into the body of the subject comprises selectively advancing a dissection tool configured to form an insertion pathway having a cross-sectional shape and size corresponding to a cross- sectional shape and size of the stimulating electrode array.

6. The method of claim 4, wherein the side edge of the stimulating electrode array comprises a distal beveled portion, and wherein the step of inserting the stimulating electrode array into the body of the subject comprises selectively advancing the stimulating electrode array to form an insertion pathway.

7. The method of claim 4, wherein the step of inserting the stimulating electrode array into the body of the subject comprises:
  providing at least one steering member having a longitudinal axis, each steering member of the at least one steering member comprising:
    an elongate housing having a distal end and an opening proximate the distal end;
    a snare means positioned within the housing and selectively extendable and retractable relative to the opening of the housing along the longitudinal axis of the steering member, wherein the snare means is configured to engage a corresponding engagement portion of the stimulating electrode array; and
    a handle comprising means for selectively deploying and retracting the snare means, the means for selectively deploying and retracting the snare means being configured for selective, one-handed activation by a user;
  selectively deploying the snare means of a first steering member of the at least one steering member such that the snare means engages a corresponding engagement portion of the stimulating electrode array; and
  selectively retracting the snare means such that the engagement portion is retained against the distal end of the housing.

8. The method of claim 7, wherein the step of selectively moving the stimulating electrode array comprises selectively moving the steering member such that the stimulating electrode array is guided to the desired position.

9. The method of claim 8, further comprising the step of disengaging the snare means from the engagement portion of the stimulating electrode array such that the stimulating electrode array remains in the desired position.

10. The method of claim 9, wherein the at least one engagement portion of the stimulating electrode array comprises a first engagement portion and a second engagement portion, and wherein the at least one steering member comprises a first steering member and a second steering member, and wherein the step of selectively deploying the snare means of a steering member comprises deploying the snare means of the first steering member such that the snare means of the first steering member engages the first engagement portion and deploying the snare means of the second steering member such that the snare means of the second steering member engages the second engagement portion.

11. The method of claim 9, wherein the elongate housing of each steering member of the at least one steering member comprises a radio-lucent material.

12. The method of claim 9, wherein the elongate housing of each steering member of the at least one steering member comprises a radio-opaque material.

13. The method of claim 9, wherein the snare means of each steering member of the at least one steering member comprises an elongate member having a retractable portion with an engagement end, and wherein the step of the selectively deploying the snare means comprises advancing the retractable portion of the snare means such that the engagement end of the retractable portion engages an engagement portion of the stimulating electrode array.

14. The method of claim 13, wherein each engagement portion of the stimulating electrode array comprises a guide loop, and wherein the step of selectively deploying the snare means comprises advancing the retractable portion of the snare means such that the engagement end of the retractable portion is received by a corresponding guide loop of the stimulating electrode array.

15. The method of claim 9, wherein each engagement portion of the stimulating electrode array protrudes outwardly from the stimulating electrode array along a respective longitudinal axis, wherein the snare means of each steering member of the at least one steering member comprises a first loop and a second loop, wherein the step of selectively deploying the snare means of a steering member comprises selectively deploying the snare means such that both the first loop and the second loop of the snare means receive an engagement portion of the stimulating electrode array.

16. The method of claim 15, wherein the step of selectively retracting the snare means comprises retracting the snare means such that the first loop and the second loop are pulled in opposing directions relative to the longitudinal axis of the engagement portion.

17. The method of claim 9, wherein the steps of selectively deploying and retracting the snare means comprises selectively advancing and retracting a thumb guide ring mounted thereon the handle of a steering member of the at least one steering member and operatively coupled to the snare means.

18. A method for optimizing stimulation of the dorsal column of the spinal cord of a subject, the method comprising:

selectively engaging a stimulating electrode array with at least one steering member, the stimulating electrode array comprising one or more electrodes and having a top surface, a bottom surface, a peripheral side edge extending between the top surface and the bottom surface, and at least one engagement portion, the peripheral side edge having a distal beveled portion configured to cut through tissue of the subject to thereby form an insertion pathway, the at least one steering member having a longitudinal axis, each steering member comprising:

an elongate housing having a distal end and an opening proximate the distal end;

a snare means positioned within the housing and selectively extendable and retractable relative to the opening of the housing along the longitudinal axis of the steering member, wherein the snare means is configured to engage a selected engagement portion of the stimulating electrode array; and a handle comprising means for selectively deploying and retracting the snare means, the means for selectively deploying and retracting the snare means being configured for selective, one-handed activation by a user, wherein the step of selectively engaging the stimulating electrode array comprises selectively deploying the snare means of a first steering member of the at least one steering member such that the snare means engages a first engagement portion of the stimulating electrode array;

selectively retracting the snare means such that the first engagement portion is retained against the distal end of the housing;

selectively moving the steering member such that the stimulating electrode array is guided to a desired position proximate the dorsal column of the spinal cord of the subject, wherein the step of selectively moving the steering member comprises forming an insertion pathway through the tissue of the subject using the distal beveled portion of the stimulating electrode array; and disengaging the snare means from the corresponding engagement portion of the stimulating electrode array such that the stimulating electrode array remains in the desired position.

* * * * *